(12) United States Patent
Boukhny et al.

(10) Patent No.: US 11,510,811 B2
(45) Date of Patent: *Nov. 29, 2022

(54) PRESSURE CONTROL IN PHACOEMULSIFICATION SYSTEM

(71) Applicant: Alcon Inc., Fribourg (CH)

(72) Inventors: Mikhail Boukhny, Laguna Niguel, CA (US); Raphael Gordon, Ladera Ranch, CA (US); Michael D. Morgan, Costa Mesa, CA (US); Gary P. Sorensen, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 301 days.

This patent is subject to a terminal disclaimer.

(21) Appl. No.: 16/898,905

(22) Filed: Jun. 11, 2020

(65) Prior Publication Data

US 2020/0297534 A1 Sep. 24, 2020

Related U.S. Application Data

(63) Continuation of application No. 16/034,941, filed on Jul. 13, 2018, now Pat. No. 10,729,581, which is a (Continued)

(51) Int. Cl.
*A61F 9/007* (2006.01)
*A61M 1/00* (2006.01)

(52) U.S. Cl.
CPC ....... *A61F 9/00745* (2013.01); *A61M 1/0058* (2013.01); *A61M 1/73* (2021.05); *A61M 1/74* (2021.05); *A61B 2217/005* (2013.01); *A61B 2217/007* (2013.01); *A61M 2205/3331* (2013.01); *A61M 2210/0612* (2013.01)

(58) Field of Classification Search
CPC .. A61F 9/007; A61F 9/00736; A61F 9/00745; A61F 9/00754; A61F 9/00763
See application file for complete search history.

(56) References Cited

U.S. PATENT DOCUMENTS 1,718,494 A 6/1929 Schurig
2,260,837 A 10/1941 Kuehni
(Continued)

FOREIGN PATENT DOCUMENTS

CA 1068572 A 12/1979
CA 1068574 A 12/1979
(Continued)

OTHER PUBLICATIONS

C.R. Bard, Inc., "Introducing Urodynamic Testing (UDT) That's as Efficient as It Is Intelligent." [Fiber optic sensor technology sales brochure.], Jan. 1994.
(Continued)

*Primary Examiner* — Kevin C Sirmons
*Assistant Examiner* — Leah J Swanson

(57) ABSTRACT

A surgical system comprises a pressurized irrigation fluid source; an irrigation line fluidly coupled to the pressurized irrigation fluid source; a hand piece fluidly coupled to the irrigation line; and a controller for controlling the pressurized irrigation fluid source. The controller controls the pressurized irrigation fluid source based on an estimated flow value modified by a compensation factor.

16 Claims, 2 Drawing Sheets

Related U.S. Application Data continuation of application No. 14/955,997, filed on Dec. 1, 2015, now Pat. No. 10,052,228, which is a continuation of application No. 14/818,762, filed on Aug. 5, 2015, now Pat. No. 9,849,030, which is a continuation of application No. 13/657,324, filed on Oct. 22, 2012, now Pat. No. 9,119,701.

(56) References Cited

U.S. PATENT DOCUMENTS

| | | |
|---|---|---|
| 2,510,073 A | 6/1950 | Clark |
| 2,583,941 A | 1/1952 | Gordon, Jr. |
| 3,805,617 A | 4/1974 | Kamazuka |
| 4,452,202 A | 6/1984 | Meyer |
| 4,475,904 A | 10/1984 | Wang |
| 4,713,051 A | 12/1987 | Steppe et al. |
| 4,750,643 A | 6/1988 | Wortrich |
| 4,758,238 A | 7/1988 | Sundblom et al. |
| 4,813,927 A | 3/1989 | Morris |
| 4,832,685 A | 5/1989 | Haines |
| 4,856,317 A | 8/1989 | Pidorenko |
| 4,892,985 A | 1/1990 | Tateishi |
| 4,900,301 A | 2/1990 | Morris |
| 4,935,005 A | 6/1990 | Haines |
| 4,963,131 A | 10/1990 | Wortrich |
| 5,032,111 A | 7/1991 | Morris |
| 5,041,096 A | 8/1991 | Beuchat et al. |
| 5,047,009 A | 9/1991 | Morris |
| 5,080,098 A | 1/1992 | Willett et al. |
| 5,098,037 A | 3/1992 | Leffel |
| 5,106,366 A | 4/1992 | Steppe |
| 5,163,900 A | 11/1992 | Wortrich |
| 5,232,439 A | 8/1993 | Campbell et al. |
| 5,267,956 A | 12/1993 | Beuchat |
| 5,282,787 A | 2/1994 | Wortrich |
| D352,106 S | 11/1994 | Fanney et al. |
| 5,364,342 A | 11/1994 | Beuchat et al. |
| 5,392,653 A | 2/1995 | Zanger et al. |
| 5,499,969 A | 3/1996 | Beuchat et al. |
| 5,520,652 A | 5/1996 | Peterson |
| D375,553 S | 11/1996 | Creed |
| 5,582,601 A | 12/1996 | Wortrich |
| 5,588,815 A | 12/1996 | Zaleski, II |
| 5,620,312 A | 4/1997 | Hyman |
| D380,550 S | 7/1997 | Dennewill et al. |
| 5,643,203 A | 7/1997 | Beiser |
| 5,676,530 A | 10/1997 | Nazarifar |
| 5,676,650 A | 10/1997 | Grieshaber et al. |
| 5,700,240 A | 12/1997 | Barwick, Jr. et al. |
| 5,747,824 A | 5/1998 | Jung et al. |
| 5,800,396 A | 9/1998 | Fanney |
| 5,830,176 A | 11/1998 | Mackool |
| 5,840,058 A | 11/1998 | Ammann |
| 5,865,764 A | 2/1999 | Moorhead |
| 5,897,524 A | 4/1999 | Wortrich et al. |
| 5,899,674 A | 5/1999 | Jung et al. |
| 6,059,544 A | 5/2000 | Jung et al. |
| 6,179,808 B1 | 1/2001 | Boukhny et al. |
| 6,261,283 B1 | 7/2001 | Morgan et al. |
| 6,293,926 B1 | 9/2001 | Sorensen et al. |
| 6,443,893 B1 | 9/2002 | Schnakenberg et al. |
| 6,491,661 B1 | 12/2002 | Boukhny |
| 6,561,999 B1 | 5/2003 | Nazarifar et al. |
| 6,572,349 B2 | 6/2003 | Sorensen et al. |
| 6,579,255 B2 | 6/2003 | Kadziauskas |
| 6,632,214 B2 | 10/2003 | Morgan |
| 6,740,074 B2 | 5/2004 | Morgan |
| 6,824,525 B2 | 11/2004 | Nazarifar |
| 6,902,542 B2 | 6/2005 | Gordon |
| 6,962,488 B2 | 11/2005 | Davis et al. |
| 7,326,183 B2 | 2/2008 | Nazarifar et al. |
| 9,119,699 B2 | 9/2015 | Gordon |
| 2002/0019607 A1 | 2/2002 | Bui |
| 2002/0033370 A1 | 3/2002 | Bainbridge |
| 2003/0028141 A1 | 2/2003 | Kadziauskas |
| 2003/0050619 A1 | 3/2003 | Mooijman |
| 2003/0108429 A1 | 6/2003 | Angelini |
| 2003/0225363 A1 | 12/2003 | Gordon |
| 2004/0253129 A1 | 12/2004 | Sorensen |
| 2005/0065462 A1 | 3/2005 | Nazarifar |
| 2005/0117117 A1 | 6/2005 | Bourla |
| 2006/0173404 A1 | 8/2006 | Urich |
| 2008/0004610 A1 | 1/2008 | Miller |
| 2008/0125697 A1 | 5/2008 | Gao |
| 2009/0048607 A1 | 2/2009 | Rockley |
| 2010/0145302 A1* | 6/2010 | Cull ......... A61M 1/0058 604/66 |
| 2010/0280435 A1 | 11/2010 | Raney |
| 2011/0202017 A1 | 8/2011 | Reimer |
| 2011/0295191 A1 | 12/2011 | Injev |
| 2011/0313343 A1 | 12/2011 | Milutinovic |
| 2012/0215160 A1 | 8/2012 | Valenti |
| 2012/0238857 A1 | 9/2012 | Wong |
| 2012/0296423 A1 | 11/2012 | Caffey |
| 2013/0138035 A1 | 5/2013 | Huculak |
| 2013/0158381 A1 | 6/2013 | Rickard |
| 2014/0275923 A1 | 9/2014 | Haffner |
| 2014/0323953 A1 | 10/2014 | Sorensen et al. |
| 2018/0028359 A1 | 2/2018 | Gordon et al. |

FOREIGN PATENT DOCUMENTS

| | | |
|---|---|---|
| CN | 1218380 A | 6/1999 |
| CN | 1239874 A | 12/1999 |
| CN | 101346112 A | 1/2009 |
| CN | 102245222 A | 11/2011 |
| CN | 102946833 A | 2/2013 |
| DE | 19852574 A1 | 5/2000 |
| EP | 0776670 B1 | 9/2001 |
| EP | 1356835 A1 | 10/2003 |
| EP | 1612532 A1 | 1/2006 |
| EP | 1895958 B1 | 8/2009 |
| JP | 2004-507321 A | 3/2004 |
| JP | 2011-177501 A | 9/2011 |
| JP | 2012-510883 A | 5/2012 |
| RU | 2434608 C1 | 11/2011 |
| RU | 112035 U1 | 1/2012 |
| RU | 2477110 C2 | 3/2013 |
| RU | 2011152000 A | 6/2013 |
| WO | 8804042 A1 | 6/1988 |
| WO | 9324817 A1 | 12/1993 |
| WO | 96/40026 A1 | 12/1996 |
| WO | 02/17833 A1 | 3/2002 |
| WO | WO-0217833 A1 * | 3/2002 ......... A61F 9/00736 |
| WO | 03/047652 A1 | 6/2003 |
| WO | 03/047653 A1 | 6/2003 |
| WO | 03/047654 A1 | 6/2003 |
| WO | WO2010054162 A2 | 5/2010 |
| WO | 2010/077563 A2 | 7/2010 |
| WO | 2012/137067 A2 | 10/2012 |

OTHER PUBLICATIONS

Kremlevsky; Chapter 1, "Differential Pressure Flowmeters. Standard Diaphragms and Nozzles"; Flowmeters and Quantity Meters Handbook 4th edition (revised and corrected); 1989; ISBN 5-217-00412-6.

Lebow Load Cell and Torque Sensor Handbook, 1989, pp. 63-99.

Nave, C.R., "Flow Resistance for a Tube", (Oct. 12, 2000), 2 pages, [retrieved from http://web.archive.org/web/20001012080238/http://hyperphysics.phy-astr.gsu.edu/hbase/pfric.htm].

Nave, C.R., "Laminar Flow", (Oct. 12, 2000), 2 pages, [retrieved from http://web.archive.org/web/20001012080238/http://hyperphysics.phy-astr.gsu.edu/hbase/pfric.htm].

* cited by examiner

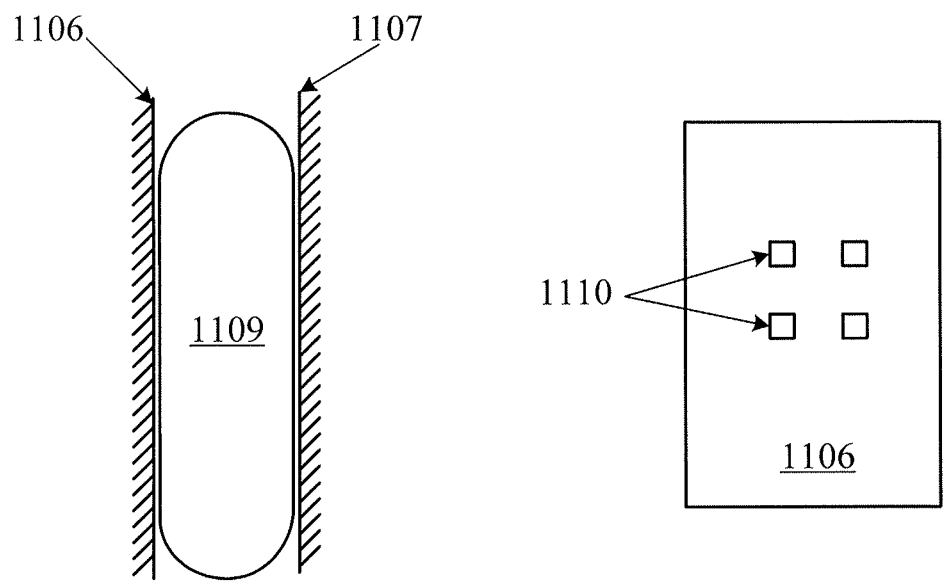
Fig. 2
Fig. 3
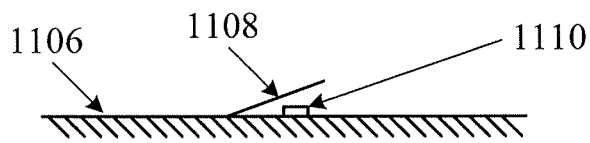
Fig. 4
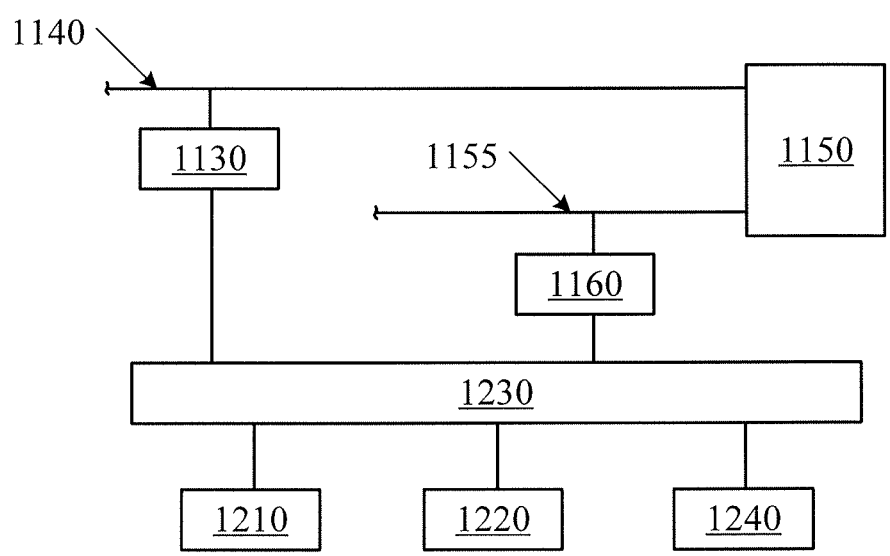
Fig. 5

PRESSURE CONTROL IN PHACOEMULSIFICATION SYSTEM

This application is a continuation of U.S. application Ser. No. 16/034,941 filed Jul. 13, 2018 which is a continuation of U.S. application Ser. No. 14/955,997 filed Dec. 1, 2015, now U.S. Pat. No. 10,052,228, which is a continuation of U.S. application Ser. No. 14/818,762 filed Aug. 5, 2015, now U.S. Pat. No. 9,849,030, which is a continuation of U.S. application Ser. No. 13/657,324 filed Oct. 22, 2012, now U.S. Pat. No. 9,119,701.

BACKGROUND OF THE INVENTION

The present invention relates to phacoemulsification surgery and more particularly to the control fluid flow during surgery.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical instrument suitable for phacoemulsification procedures on cataractous lenses includes an ultrasonically driven phacoemulsification hand piece, an attached hollow cutting needle surrounded by an irrigating sleeve, and an electronic control console. The hand piece is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece.

During a phacoemulsification procedure, the tip of the cutting needle and the end of the irrigation sleeve are inserted into the anterior segment of the eye through a small incision in the eye's outer tissue. The surgeon brings the tip of the cutting needle into contact with the lens of the eye, so that the vibrating tip fragments the lens. The resulting fragments are aspirated out of the eye through the interior bore of the cutting needle, along with irrigation fluid provided to the eye during the procedure, and into a waste reservoir.

Throughout the procedure, irrigating fluid is infused into the eye, passing between the irrigation sleeve and the cutting needle and exiting into the eye at the tip of the irrigation sleeve and/or from one or more ports or openings formed into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

Conventional systems employ fluid-filled bottles or bags hung from an intravenous (IV) pole as an irrigation fluid source. Irrigation flow rates, and corresponding fluid pressure at the eye, are regulated by controlling the height of the IV pole above the surgical site. For example, raising the IV pole results in a corresponding increase in head pressure and increase in fluid pressure at the eye, resulting in a corresponding increase in irrigation flow rate. Likewise, lowering the IV pole results in a corresponding decrease in pressure at the eye and corresponding irrigation flow rate to the eye.

Aspiration flow rates of fluid from the eye are typically regulated by an aspiration pump. The pump action produces aspiration flow through the interior bore of the cutting needle. The aspiration flow results in the creation of vacuum at the aspiration line. The aspiration flow and/or vacuum are set to achieve the desired working effect for the lens removal. The IV pole height and irrigation pump are regulated to achieve a proper intra-ocular chamber balance in an effort to maintain a relatively consistent fluid pressure at the surgical site within the eye.

While a consistent fluid pressure in the eye is desirable during the phacoemulsification procedure, a common phenomenon during a phacoemulsification procedure arises from the varying flow rates that occur throughout the surgical procedure. Varying flow rates result in varying pressure losses in the irrigation fluid path from the irrigation fluid supply to the eye, thus causing changes in pressure in the anterior chamber (also referred to as Intra-Ocular Pressure or IOP). Higher flow rates result in greater pressure losses and lower IOP. As IOP lowers, the operating space within the eye diminishes.

Another common complication during the phacoemulsification process arises from a blockage, or occlusion, of the aspirating needle. As the irrigation fluid and emulsified tissue is aspirated away from the interior of the eye through the hollow cutting needle, pieces of tissue that are larger than the diameter of the needle's bore may become clogged in the needle's tip. While the tip is clogged, vacuum pressure builds up within the tip. The resulting drop in pressure in the anterior chamber in the eye when the clog is removed is known as post-occlusion surge. This post-occlusion surge, in some cases, can cause a relatively large quantity of fluid and tissue to be aspirated out of the eye too quickly, potentially causing the eye to collapse and/or causing the lens capsule to be torn.

Various techniques have been attempted to reduce this surge, such as by venting the aspiration line or otherwise limiting the buildup of negative pressure in the aspiration system. However, there remains a need for improved phacoemulsification devices, including irrigation systems that reduce post-occlusion surge as well as maintain a stable IOP throughout varying flow conditions.

SUMMARY OF THE INVENTION

In one embodiment consistent with the principles of the present invention, the present invention is a surgical system comprising a pressurized irrigation fluid source; an irrigation line fluidly coupled to the pressurized irrigation fluid source; a hand piece fluidly coupled to the irrigation line; an irrigation pressure senor located at or along the pressurized irrigation fluid source or irrigation line; and a controller for controlling the pressurized irrigation fluid source. The controller controls the pressurized irrigation fluid source based on a reading from the irrigation pressure sensor and an estimated flow value modified by a compensation factor.

The surgical system may also include a display and a controller input device. The controller input device may receive a desired intraocular pressure value and the controller may control the pressurized irrigation fluid source so as to maintain the desired intraocular pressure value. The controller input device may receive a desired intraocular pressure range and the controller may control the pressurized irrigation fluid source so as to maintain the desired intraocular pressure range. The controller may calculate intraocular pressure of an eye based on the reading from the irrigation pressure sensor, a source pressure sensor, or the aspiration pressure sensor, or from the estimated flow value modified by the compensation factor. The controller may also calculate the estimated flow value based on a reading from the irrigation pressure sensor, the source pressure sensor, and an impedance of the irrigation line.

The system may also include an aspiration line fluidly coupled to the hand piece; an aspiration pressure sensor located at or along the aspiration line; and an aspiration pump configured to draw fluid through the aspiration line. In such a case, the controller may calculate the estimated flow value based on a reading from the aspiration pressure sensor, a maximum pump vacuum achievable by the aspiration pump, and an impedance of the aspiration pump.

The system may also include a flexible bag holding a fluid and two opposing plates. The flexible bag can be located between the two opposing plates. In such a case, the controller may calculate the estimated flow value based on travel or motion of the two opposing plates.

In some embodiments, the compensation factor may be based on incision leakage and/or sleeve compression, a needle and sleeve selected for a procedure, or flow characteristics of the needle and sleeve combination. The controller input device may receive needle and sleeve information and the controller uses the needle and sleeve information to select or calculate the compensation factor. The controller input device may receive the compensation factor as an input from the user.

The controller may use a reading from the aspiration pressure sensor to determine if an occlusion is present or if an occlusion break occurs. In such a case, the controller may control the pressurized irrigation fluid source to accommodate for changes in fluid flow that result from the occlusion or the occlusion break. The controller may use a reading from the irrigation pressure sensor to determine if an occlusion is present or if an occlusion break occurs. In such a case, the controller may control the pressurized irrigation fluid source to accommodate for changes in fluid flow that result from the occlusion or the occlusion break.

In other embodiments of the present invention, a surgical system comprises: a pressurized irrigation fluid source, the pressurized irrigation fluid source comprising a flexible bag located between two opposing plates, the flexible bag containing a fluid; a position sensor located at or on one of the two opposing plates, the position sensor for determining a distance between the two opposing plates; an actuator for moving at least one of the two opposing plates so as to squeeze the flexible bag; and a controller for controlling the relative movement of the opposing plates. The controller receives reading from the position sensor, determines the distance between the plates, and provides an estimate of an amount of fluid in the flexible bag.

In other embodiments of the present invention, a surgical system comprises: a pressurized irrigation fluid source, the pressurized irrigation fluid source comprising a flexible bag located between two opposing plates, the flexible bag containing a fluid, a hinged plate located on a surface of one of the two opposing plates; a source pressure sensor located between a face of the hinged plate and a face of one of the two opposing plates, such that the face of the hinged plate presses the source pressure sensor against the face of one of the two opposing plates.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

In one embodiment consistent with the principles of the present invention, a method of controlling a surgical system having a fluid flow path comprises: receiving a pressure reading from an irrigation pressure sensor located along the fluid flow path; calculating an estimated fluid flow through the surgical system; modifying the estimated fluid flow with a compensation factor; and controlling a pressurized irrigation fluid source based on the pressure reading and the estimated fluid flow as modified by the compensation factor.

In other embodiments of the present invention, the method may also comprise one or more of the following: receiving a desired intraocular pressure value; and controlling the pressurized irrigation fluid source so as to maintain the desired intraocular pressure value; receiving a desired intraocular pressure range; and controlling the pressurized irrigation fluid source so as to maintain the desired intraocular pressure range; calculating an intraocular pressure of an eye based on the reading from the irrigation pressure sensor; calculating an intraocular pressure of an eye based on the estimated flow value modified by the compensation factor; receiving a reading from an aspiration pressure sensor located along the fluid path, a maximum pump vacuum achievable by the aspiration pump, and an impedance of the aspiration pump; and estimating flow based on a difference between the reading from the aspiration pressure sensor and the maximum pump vacuum achievable by the aspiration pump; receiving a reading from the irrigation pressure sensor, a reading from a source pressure sensor, and an impedance of the fluid flow path between the source pressure sensor and the irrigation pressure sensor; and estimating flow based on a difference between the reading from the irrigation pressure sensor and the source pressure sensor; receiving a compensation factor from a user; receiving needle and sleeve information; and using the needle and sleeve information to select or calculate the compensation factor; receiving a pressure reading from an aspiration pressure sensor located along the fluid path; and using the pressure reading from the aspiration pressure sensor to determine if an occlusion is present or if an occlusion break occurs; accommodating for changes in fluid flow that result from the occlusion or the occlusion break; receiving a pressure reading from the irrigation pressure sensor; and using the pressure reading from the irrigation pressure sensor to determine if an occlusion is present or if an occlusion break occurs.

In other embodiments consistent with the principles of the present invention, a method of calculating incision leakage comprises: calculating irrigation fluid flow; calculating aspiration fluid flow; and subtracting calculated aspiration fluid flow from calculated irrigation fluid flow; wherein calculated irrigation fluid flow and calculated aspiration fluid flow are determined from differential pressure measurements.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is a pressurized irrigation fluid source according to the principles of the present invention.

FIGS. 3 and 4 depict a hinged pressure sensor arrangement for a pressurized irrigation fluid source according to the principles of the present invention.

FIG. 5 is a diagram of system components in a pressurized irrigation fluid source control system.

DETAILED DESCRIPTION OF THE PREFERRED EMBODIMENTS

Figure 1:
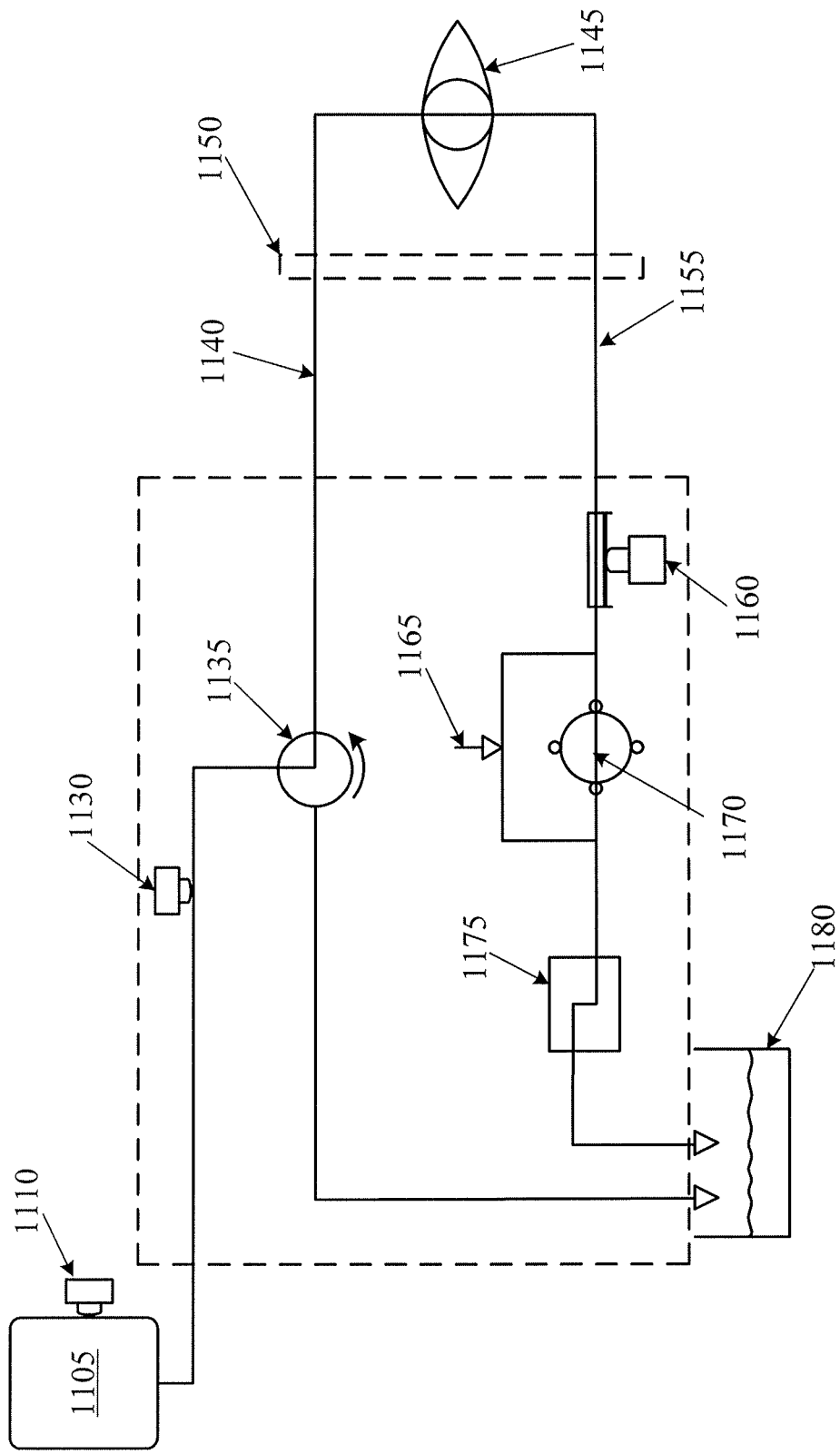
FIG. 1 is a diagram of the components in the fluid path of a phacoemulsification system including a pressurized irrigation source according to the principles of the present invention.

Reference is now made in detail to the exemplary embodiments of the invention, examples of which are illustrated in the accompanying drawings. Wherever possible, the same reference numbers are used throughout the drawings to refer to the same or like parts.

FIG. 1 is a diagram of the components in the fluid path of a phacoemulsification system including a pressurized irrigation source according to the principles of the present invention. FIG. 1 depicts the fluid path through the eye 1145 during cataract surgery. The components include a pressurized irrigation fluid source 1105, a source pressure sensor 1110, an irrigation pressure sensor 1130, a three-way valve 1135, an irrigation line 1140, a hand piece 1150, an aspiration line 1155, an aspiration pressure sensor 1160, a vent valve 1165, a pump 1170, a reservoir 1175 and a drain bag 1180. The irrigation line 1140 provides irrigation fluid to the eye 1145 during cataract surgery. The aspiration line 1155 removes fluid and emulsified lens particles from the eye during cataract surgery.

When irrigation fluid exits pressurized irrigation fluid source 1105, it travels through irrigation line 1140 and into the eye 1145. An irrigation pressure sensor 1130 measures the pressure of the irrigation fluid in irrigation line 1140. Irrigation pressure sensor 1130 may be located anywhere along the irrigation line 1140 or irrigation fluid path. If located close to the eye 1145, irrigation pressure sensor may also be incorporated into the irrigation path of the hand piece 1150. In some instances, the irrigation line 1140 may pass through and include a path in a fluidics cassette. In this case, the irrigation pressure sensor 1130 may be located in the fluidics cassette. For purposes of this description, irrigation line 1140 may comprise flexible tubing, a path through a fluidics cassette, rigid tubing, or other fluidic pathways that carry irrigation fluid from pressurized irrigation fluid source 1105 through hand piece 1150 and into eye 1145. Source pressure sensor 1110 also measures the pressure of irrigation fluid at the pressurized irrigation fluid source 1105. A three-way valve 1135 is provided for on/off control of irrigation and to provide a path to the drain bag 1180. Irrigation pressure sensor 1130 and source pressure sensor 1110 are implemented by any of a number of commercially available fluid pressure sensors. Irrigation pressure sensor 1130 and/or source pressure sensor 1110 provides pressure information to a controller (shown in FIG. 5) that operates pressurized irrigation fluid source 1105. The pressurized irrigation fluid source 1105 controls the pressure and/or flow rate of the irrigation fluid exiting it.

In some embodiments of the present invention, the pressurized irrigation fluid source 1105 includes a flexible bag that contains irrigation fluid. In this case, the bag can be squeezed to pressurize the fluid it contains. For example, the bag may be located between two opposing plates that press together to pressurize the contents of the bag (as more fully described in FIG. 2). In another example, a flexible band surrounds the bag and is tightened to squeeze the bag and pressurize its contents. In other embodiments of the present invention, the pressurized irrigation fluid source 1105 includes a bottle or other container that can be pressurized. In further embodiments of the present invention, the pressurized irrigation fluid source 1105 is pressurized using a pump or a compressed gas.

The source pressure sensor 1110 may be a single pressure sensor or an array of pressure sensors. The source pressure sensor 1110 may contact the pressurized irrigation fluid source 1105 to determine the pressure of its contents. For example, when the pressurized irrigation fluid source 1105 is a flexible bag located between two opposing plates, source pressure sensor 1110 may be located on one of the plates adjacent to the bag. As the plates travel, the bag is pressurized and source pressure sensor 1110 measures the pressure. In this case, the source pressure sensor 1110 may be an array of sensors located on the plate or a single sensor located on the plate. In another example, a hinged plated may be used as more fully described in FIG. 4.

FIG. 2 depicts pressurized irrigation fluid source 1105 as a flexible bag 1109 (e.g. an IV bag) located between two opposing plates 1106 and 1107. One of the two plates 1106 or 1107 may be fixed while the other plate travels to compress or squeeze flexible bag 1109. For example, plate 1106 may be fixed and plates 1107 may travel to compress flexible bag 1109. In FIG. 3, plate 1106 has an array of source pressure sensors 1110 located on a surface that faces the flexible bag 1109. In this manner, a reading from each of the four depicted source pressure sensors 1110 may lead to a more accurate pressure reading. In this example, a reading can be taken from each of the four source pressure sensors 1110, and the readings averaged or an errant reading thrown out. In FIG. 4, a source pressure sensor 1110 (or an array of sensors) is located on plate 1106 under a hinged plate 1108. The flat surface of the hinged plate 1108 contacts the source pressure sensor 1110. In some cases, the surface of the flexible bag 1109 may become wrinkled or have creases when it is squeezed between plates 1106 and 1107. These wrinkles or creases can lead to inaccurate pressure readings if a wrinkle or crease is located at a source pressure sensor 1110. Using an array of sensors as shown in FIG. 3 is one way to overcome this problem. Using a hinged plate 1108 is another way. When using a hinged plate 1108, a flat uniform surface always contacts source pressure sensor 1110.

FIG. 5 is a block diagram representing some components of a phacoemulsification machine. FIG. 5 shows an irrigation line 1140, an irrigation pressure sensor 1130 in, along, or associated with the irrigation line 1140, an aspiration line 1155, an aspiration pressure sensor 1160 in, along, or associated with the aspiration line 1155, a hand piece 1150, a controller 1230, a flow command input device 1210 (e.g. a foot pedal), a display 1220, and an associated controller input device 1240 for entering data or commands for programming the system.

The irrigation line 1140 extends between a pressurized irrigation fluid source 1105 and the hand piece 1150 and carries fluid to the hand piece 1150 for irrigating an eye during a surgical procedure (as shown in FIG. 1). In one example, the sterile fluid is a saline fluid, however, other fluids may be used. At least a portion of the irrigation line 1140 may be formed of a flexible tubing, and in some embodiments, the path 1140 is formed of multiple segments, with some segments being rigid and others being flexible.

The irrigation pressure sensor 1130 is associated with the irrigation line 1140 and performs the function of measuring the irrigation pressure in the irrigation line 1140. In some embodiments, the sensor 1130 is a pressure sensor configured to detect current pressure conditions. The sensor 1130 communicates signals indicative of the sensed pressure to the controller 1230. Once received, the controller 1230 processes the received signals to determine whether the measured pressure is above or below a desired pressure or within a pre-established desired pressure range. Although described as a pressure sensor, the irrigation pressure sensor 1130 may be another type of sensor, such as a flow sensor that detects actual fluid flow and may include additional sensors for monitoring additional parameters. In some embodiments, the sensor 1130 includes its own processing function and the processed data is then communicated to the controller 1230.

The aspiration line 1155 extends from the hand piece to the drain reservoir 1180 (as shown in FIG. 1). The aspiration line 1155 carries away fluid used to flush the eye as well as any emulsified particles.

The aspiration pressure sensor 1160 is associated with the aspiration line 1155 and performs the function of measuring the waste fluid pressure in the aspiration line 1155. Like the sensor 1130 described above, the sensor 1160 may be a pressure sensor configured to detect current pressure conditions. It communicates signals indicative of the sensed pressure to the controller 1230. The sensor 1160, like the sensor 1130, may be any suitable type of sensor, such as a flow sensor that detects actual fluid flow and may include additional sensors for monitoring additional parameters.

The hand piece 1150 may be an ultrasonic hand piece that carries the irrigation fluid to the surgical site. The hand piece is configured as known in the art to receive and operate with different needles or equipment depending on the application and procedure being performed. It should be noted that although an ultrasonic hand piece is discussed, the principles of the invention are intended to cover the use of vitrectomy cutter hand pieces or other hand pieces known in the art. For ease of reference only, this application will refer only to the hand piece 1150, recognizing that the system operates in a similar manner with other hand pieces.

In the example shown, the fluid command input device 1210 is typically a foot pedal. It can receive inputs indicative of a desired flow rate, desired pressure, or other fluid characteristic. It is configured to control the operational setting of the machine through a plurality of major control settings, including controlling the irrigation flow rate or pressure within each of the major control settings. In some embodiments, the flow command input device is not a foot pedal, but is another input device, located elsewhere on the machine.

The controller input device 1240 permits a user to enter data or commands that affect system programming. In this embodiment, the controller input device 1240 is associated with the display 1220. However, it could be associated directly with the controller in a manner known in the art. For example, in some embodiments, the controller input device 1240 is a standard computer keyboard, a standard pointing device, such as a mouse or trackball, a touch screen or other input device.

As is apparent from FIG. 5, the controller 1230 communicates with the display 1220, the flow command input device 1210, the hand piece 1150, the irrigation pressure sensor 1130, the aspiration pressure sensor 1160, and the controller input device 1240. It is configured or programmed to control the pressurized irrigation system based upon pre-established programs or sequences.

In use, the controller 1230 is configured to receive signals from the irrigation pressure sensor 1130 and process the signals to determine whether the detected irrigation pressure is outside of an acceptable range or above or below acceptable thresholds. If the controller 1230 detects an unacceptable irrigation pressure, it controls the pressurized irrigation system to correct the pressure to a desired range. Likewise, in another example, the controller 1230 is configured to receive signals from the aspiration pressure sensor 1160 and process the signals to determine whether the detected pressure is outside of an acceptable range or above or below acceptable thresholds. If the controller 1230 detects an unacceptable pressure, it controls the pressurized irrigation system to correct the pressure to a desired range. In this manner, the irrigation pressure sensor 1130 and/or the aspiration pressure sensor 1160 may be used to control the fluid pressure in the eye (IOP).

Returning to FIG. 1, aspiration pressure sensor 1160 measures the pressure in the aspiration line 1155 or aspiration pathway. Aspiration pressure sensor 1160 may be located anywhere along the aspiration line 1155 or aspiration pathway. If located close to the eye 1145, aspiration pressure sensor may be located in the hand piece 1150. Aspiration pressure sensor 1160 is implemented by any of a number of commercially available fluid pressure sensors. Aspiration pressure sensor 1160 provides pressure information to a controller (shown in FIG. 5) that operates pressurized irrigation fluid source 1105.

A hand piece 1150 is placed in the eye 1145 during a phacoemulsification procedure. The hand piece 1150 has a hollow needle that is ultrasonically vibrated in the eye to break up the diseased lens. A sleeve located around the needle provides irrigation fluid from irrigation line 1140. The irrigation fluid passes through the space between the outside of the needle and the inside of the sleeve. Fluid and lens particles are aspirated through the hollow needle. In this manner, the interior passage of the hollow needle is fluidly coupled to aspiration line 1155. Pump 1170 draws the aspirated fluid from the eye 1145. An aspiration pressure sensor 1160 measures the pressure in the aspiration line. An optional vent valve can be used to vent the vacuum created by pump 1170. The aspirated fluid passes through reservoir 1175 and into drain bag 1180.

During a phacoemulsification procedure, the tip of the needle on hand piece 1150 may become occluded with a lens particle. This creates a condition that is called an occlusion. During an occlusion, less fluid is generally aspirated from the eye, and the vacuum pressure in aspiration line 1155 increases as a result of the occlusion. Accordingly, during an occlusion, aspiration pressure sensor 1160 detects the increased vacuum that is present in aspiration line 1155. When the occlusion breaks (that is when the lens particle that causes the occlusion is broken up by the ultrasonic needle), a surge occurs. The increased vacuum in aspiration line 1155 creates a sudden demand for fluid from the eye resulting in a rapid lowering of IOP and shallowing of the operating space within the eye. This can lead to a dangerous situation in which various structures of the eye can be damaged.

Upon occlusion break, the aspiration pressure sensor 1160 detects a drop in pressure in aspiration line 1155. Likewise, the irrigation pressure sensor 1130 also detects the pressure drop in irrigation line 1140 that occurs as a result of occlusion break. Signals from the irrigation pressure sensor 1130 and/or the aspiration pressure sensor 1160 may be used by the controller 1230 to control the irrigation source 1105 as more thoroughly described below.

The pressurized irrigation system of the present invention is capable of responding to the surge caused by occlusion break by increasing the irrigation pressure in irrigation line 1140. When an occlusion breaks and a surge occurs, pressurized irrigation fluid source 1105 increases the pressure of the irrigation fluid in response. Increasing the irrigation pressure of pressurized irrigation fluid source 1105 meets the added fluid demand caused by occlusion break. In this manner, the pressure and resulting operating space in eye 1145 can be maintained at a relatively constant value which may be selected by the surgeon.

Likewise, when an occlusion occurs, irrigation pressure may increase as the fluid aspirated from the eye decreases. An increase in irrigation fluid pressure detected by irrigation pressure sensor 1130 can be used to control pressurized irrigation fluid source 1105 to regulate the pressure in eye 1145—that is to keep the pressure in eye 1145 within an acceptable range. In such a case, the aspiration pressure sensor 1160 may also detect the presence of an occlusion and a reading from it may be used by controller 1230 to control pressurized irrigation source 1105. In this case, the pressure in pressurized irrigation fluid source 1105 is not increased but remains the same or is decreased.

Generally, control of the pressurized irrigation fluid source 1105 is based on two parameters: (1) a pressure reading and (2) an estimate of irrigation flow based on flow through the system (or a measurement of actual flow through the system). The pressure reading may be from the irrigation pressure sensor 1130 (i.e. pressure in the irrigation line), the aspiration pressure sensor 1160 (i.e. pressure in the aspiration line) or the source pressure sensor 1110 (i.e. pressure at the pressurized irrigation source).

In one embodiment of the present invention, control of the pressurized irrigation fluid source 1105 can be based on irrigation pressure and flow through the system as modified by the compensation factor (as described in detail below). Irrigation pressure can be used to control for occlusion break and to maintain a constant IOP. Irrigation flow also determines IOP. Flow through the system as modified by the compensation factor (which equates to irrigation flow) can be used to control for incision leakage and sleeve compression. Collectively, these parameters can be used to maintain a constant IOP during the procedure.

Estimated flow through the system is generally the fluid flow from the pressurized irrigation source 1105 through the irrigation line 1140, through the hand piece 1150, into the eye 1145, out of the eye 1145, through the hand piece 1150, through the aspiration line 1155 and into the drain bag 1180. In operation, fluid may also be lost from the system by leakage from the eye 1145 or the wound through which the needle of the hand piece 1150 is inserted (also called "incision leakage"). In this manner the total fluid flow in the system is equal to the fluid that flows through the eye minus the fluid that is lost due to incision leakage.

Estimated fluid flow may be based on a number of different calculations. For example, flow can be estimated by any of the following:

(1) A differential pressure measurement to calculate flow can be based on an aspiration pressure sensor reading plus pump impedance plus maximum vacuum attained by the aspiration pump. Flow can be calculated by the difference between the measured aspiration pressure at the aspiration pressure sensor 1160, the maximum vacuum that can be created by the pump 1170, and the pump impedance. The impedance of the pump 1170 is a known parameter and the maximum vacuum that the pump creates can be measured accurately as can the aspiration pressure (by the aspiration pressure sensor 1160). In this manner, flow is estimated by the difference in two pressures in the fluid path and the impedance of that path. In this case, the two pressures are the pressure measure by the aspiration pressure sensor 1160 and the maximum pressure achievable by the pump 1170. The impedance in this example is the impedance of the pump 1170.

(2) A differential pressure measurement to calculate flow can be based on the source pressure measured at the source pressure sensor 1110, the irrigation pressure measured at the irrigation pressure sensor 1130, and the impedance of the irrigation line (or irrigation path) from the irrigation source 1105 to the irrigation pressure sensor 1130. Flow can be calculated by the pressure difference between the irrigation source 1105 and the irrigation pressure sensor 1130 and the impedance of the irrigation line 1140 between the irrigation source and the irrigation pressure sensor. In this manner, flow is estimated by the difference in two pressures in the fluid path and the impedance of that path.

(3) When the pressurized irrigation fluid source 1105 is a flexible bag 1109 located between two opposing plates 1106 and 1107 (as depicted in FIG. 2), the travel of plates 1106 and 1107 correspond to fluid flow through the system. Fluid flow and/or the volume of fluid used during the procedure can be estimated directly from the position of plates 1106 and 1107. Generally, during a procedure, plates 1106 and 1107 travel toward each other to squeeze fluid out of flexible bag 1109 at a desired pressure or flow rate. The total fluid that exits the flexible bag 1109 is directly related to the position of the opposing plates 1106 and 1107. The closer plates 1106 and 1107 are together, the more fluid has left the flexible bag 1109. In this manner, the position of plates 1106 and 1107 can also be used to indicate the amount of fluid left in the flexible bag 1109 and provide an indication to the surgeon of the fluid level in the flexible bag 1109 (for example, by displaying fluid level on the display 1220).

Actual fluid flow through the system may also be affected by two different factors: incision leakage and sleeve compression. As noted above, the hand piece 1150 has a sleeve located around a needle. The sleeve provides irrigation fluid from irrigation line 1140 to the eye 1145. The irrigation fluid passes through the space between the outside of the needle and the inside of the sleeve. Fluid and lens particles are aspirated through the hollow needle. During a procedure, the sleeve and needle are inserted into the eye through a small incision. In this manner, the sleeve contacts the eye tissue of the incision (or wound). Incision leakage describes the amount of fluid that exits the eye through the wound (or through the space between the sleeve and the eye tissue through which the wound is formed). During a procedure, fluid may exit the eye through the wound—such fluid loss exits the system (i.e. the fluid that exits the eye does not pass through the aspiration line 1155). Incision leakage typically results in the loss of a small amount of fluid thus decreasing the total flow through the system. Expressed mathematically, irrigation flow=aspiration flow+incision leakage.

Sleeve compression generally describes the condition in which the sleeve is pinched or compressed against the needle when inserted into the incision. Sleeve compression occurs more frequently with smaller incisions and may or may not result in less incision leakage. Sleeve compression can restrict fluid flow through the system. Since pinching the sleeve increases the flow resistance in the system, flow may be decreased when sleeve compression is present.

Generally, the losses due to incision leakage and sleeve compression are dependent on the type of needle and sleeve that is being used as well as surgeon technique. Flow profiles for various combinations of needles and sleeves can be determined experimentally and the resulting data incorporated into an algorithm or database for use in control of pressurized irrigation fluid source 1105. Alternatively, such experimental data can be aggregated to provide a range of different compensation factors (as described in the next paragraph). Surgeon technique differs considerably among the population of ophthalmologists. During a procedure, some surgeons may move the needle in a manner that creates more sleeve compression. Surgeons also prefer different sizes of needles and sleeves as well as different incision sizes. These surgeon specific factors also impact incision leakage and sleeve compression.

A compensation factor may be implemented to compensate for these two different variables that result in a decrease in flow through the system: incision leakage and sleeve compression. Incision leakage may be compensated with an estimated incision leak rate factor (which can be implemented as an offset that is set as a default value). Sleeve compression may be compensated with an estimated compression factor. The incision leak rate factor and the sleeve compression factor may collectively comprise the compensation factor. The compensation factor may be surgeon-adjustable. The compensation factor may be an offset that acts to either increase or decrease the pressure at the pressurized irrigation fluid source 1105. For example, the compensation factor may be an integer from zero to seven (with zero being no compensation and seven being maximum compensation).

Irrigation flow can be estimated from the estimated flow through the system and the compensation factor. Since irrigation flow generally equals aspiration flow plus incision leakage. Therefore, irrigation pressure can be estimated from the compensation factor and estimated flow through the system.

Generally, in order to compensate for the decreased flow (or losses) resulting from incision leakage and sleeve compression, the pressure in pressurized irrigation fluid source 1105 is increased slightly. Such increase in pressure may be implemented in an algorithm based on the compensation factor. In the above example, a surgeon may select a compensation factor of three to provide moderate compensation for incision leakage and sleeve compression. In this example, a compensation factor setting of three may correspond to a slight increase in pressure at the pressurized irrigation fluid source 1105. In other words, the baseline pressure at the pressurized irrigation fluid source 1105 is increased slightly to compensate for these factors.

In another example, the compensation factor may be implemented by a default offset value that can be adjusted by the surgeon. A nominal constant may be the default offset value in the algorithm. The surgeon may adjust this default value by a factor (of between zero for no compensation and 2 for double the compensation). The default offset value can be determined by the experimental data relating to flow characteristics of various needle and sleeve combinations. Some needle and sleeve combinations are much more common than others, so that the most common combinations may be used to determine the default offset value. In other instances, an aggregation of this data may be used to determine the default offset value.

In another example, the surgeon may enter the type of sleeve and needle via controller input device 1240. A bar code reader may be employed to scan the bar code from the surgical pack that includes the sleeve and needle as well. When the controller 1230 receives the needle and sleeve information, it can determine the flow characteristics associated with needle and sleeve (or look up the flow characteristics from a database) and select an appropriate compensation factor. In addition, doctor preferences and/or data from prior procedures can be used to select the proper compensation factor. For example, parametric data from prior procedures may be used to determine doctor technique and adjust, modify, or select the compensation factor.

Regardless of how the compensation factor is determined, the compensation factor may be used to compensate for flow losses. The compensation factor may be used to control the pressurized irrigation fluid source 1105 so as to provide an amount of fluid equal to that fluid lost due to incision leakage. The compensation factor may be used to control the pressurized irrigation fluid source 1105 so as to provide a slight increase in pressure to overcome the increased flow resistance caused by sleeve compression. In addition, since irrigation flow determines IOP, the compensation factor is used to adjust IOP as well as to compensate for flow losses.

Therefore, control of the pressurized irrigation fluid source 1105 can be based on irrigation pressure and flow through the system as modified by the compensation factor. Irrigation pressure can be used to control for occlusion break and to maintain a relatively constant IOP. Flow through the system as modified by the compensation factor can be used to compensate for incision leakage and sleeve compression and maintain a relatively constant IOP. Collectively, these parameters can be used to maintain a relatively constant IOP during the procedure.

The estimation of IOP may be based on the irrigation pressure sensor. The pressure drop between the irrigation pressure sensor and the eye is known because the characteristics of the passage between the irrigation pressure sensor and the eye are known. For example, if the irrigation pressure sensor is located in a fluidics cassette that is connected to the hand piece 1150 through a length of irrigation line 1140, then the flow impedance of the length of irrigation line 1140 and the irrigation pathway through the hand piece 1150 are both known (or can be measured). IOP can then be determined from the irrigation pressure sensor reading. The IOP reading may also be affected by sleeve compression (because the sleeve is in the irrigation path between the irrigation pressure sensor and the eye) and incision leakage. The compensation factor may be used to adjust IOP for these losses (or changes in the impedance).

In one embodiment of the present invention, a surgeon selects a desired IOP. The pressurized irrigation fluid source 1105 is then controlled to maintain the desired IOP. Since IOP is based on a reading from the irrigation pressure sensor, the irrigation pressure sensor 1130 can be used to control the pressurized irrigation fluid source 1105. In conjunction with irrigation pressure, flow through the system as modified by the compensation factor can also be used to control the pressurized irrigation fluid source 1105. Irrigation flow also determines IOP. The flow through the system as modified by compensation factor equates to irrigation flow. When an occlusion is present (as detected by the irrigation pressure sensor 1130 or the aspiration pressure sensor 1160), IOP can be maintained by this control scheme. On occlusion break (as detected by the irrigation pressure sensor 1130 or the aspiration pressure sensor 1160), the pressurized irrigation fluid source 1105 can be controlled to maintain a relatively constant IOP.

Alternatively, source pressure sensor 1110 or aspiration pressure sensor 1160 may be used in place of irrigation pressure sensor 1130 in the control scheme above.

The control of pressurized irrigation fluid source 1105 can also be described in three different states: steady state (when the needle is not occluded and flow through the system is relatively constant); occluded state (when the needle is occluded and there is little or no flow through the system); and occlusion break or surge (when there is a sudden and rapid flow through the system). An example of each state is described.

For example, in steady state, the pressurized irrigation fluid source 1105 is controlled to maintain a selected IOP. The irrigation pressure sensor 1130 is used to provide an estimate of IOP. A pressure reading from irrigation pressure sensor 1130 is received by the controller 1230. The desired IOP is also received by the controller 1230. The controller directs the operation of pressurized irrigation fluid source 1105 so as to maintain the desired IOP. In steady state, the controller typically directs pressurized irrigation fluid source 1105 to provide fluid at a relatively constant pressure to maintain IOP. In addition, the controller calculates a value for estimated fluid flow as modified by the compensation factor. In this example, in steady state, flow may be estimated by a differential pressure measurement or by plate travel. In the case of a differential pressure measurement, the controller 1230 receives the pressure reading(s) needed for the differential pressure measurement and makes the calculation. In the case of plate travel, the controller 1230 receives readings from position sensors or the like and determines plate travel. The compensation factor is also received by the controller (as an input by the surgeon, for example). Since irrigation fluid flow (estimated flow through the system as modified by the compensation factor) is related to IOP, the controller 1230 directs the operation of pressurized irrigation fluid source 1105 to maintain a flow rate consistent with the desired IOP. The net result is that the compensation factor is used to adjust fluid pressure at the pressurized irrigation fluid source 1105 to compensate for flow losses.

When an occlusion occurs, the tip of the needle is wholly or partially clogged with a lens particle. In the occluded state, flow through the system is decreased. The irrigation pressure sensor 1130 provides an estimate of IOP. A pressure reading from irrigation pressure sensor 1130 is received by the controller 1230. The desired IOP is also received by the controller 1230. The controller directs the operation of pressurized irrigation fluid source 1105 so as to maintain the desired IOP. In an occluded state, the controller typically directs pressurized irrigation fluid source 1105 to provide fluid at a relatively constant pressure to maintain IOP. Maintaining pressure in an occluded state is likely to mean that the plates 1106 and 1107 maintain the flexible bag 1109 at a relatively constant pressure. In addition, the controller calculates a value for estimated fluid flow as modified by the compensation factor as detailed above. Since irrigation fluid flow (estimated flow through the system as modified by the compensation factor) is related to IOP, the controller 1230 directs the operation of pressurized irrigation fluid source 1105 to maintain a flow rate consistent with the desired IOP. The net result is that the compensation factor is used to adjust fluid pressure at the pressurized irrigation fluid source 1105 to compensate for flow losses (e.g. incision leakage).

When an occlusion break occurs, the lens particle at the tip of the needle is dislodges and a surge of fluid exist the eye through the lumen of the needle. During occlusion break, flow through the system is increased. The irrigation pressure sensor 1130 provides an estimate of IOP. A pressure reading from irrigation pressure sensor 1130 is received by the controller 1230. The desired IOP is also received by the controller 1230. The controller directs the operation of pressurized irrigation fluid source 1105 so as to maintain the desired IOP. During occlusion break, the controller typically directs pressurized irrigation fluid source 1105 to provide fluid at an increased pressure to maintain IOP. Maintaining pressure during occlusion break is likely to mean that the plates 1106 and 1107 exert force on the flexible bag 1109 to increase the pressure in the irrigation line so as to provide the necessary fluid flow to meet the fluid demand of the surge. In addition, the controller calculates a value for estimated fluid flow as modified by the compensation factor as detailed above. Since irrigation fluid flow (estimated flow through the system as modified by the compensation factor) is related to IOP, the controller 1230 directs the operation of pressurized irrigation fluid source 1105 to maintain a flow rate consistent with the desired IOP. The net result is that the compensation factor is used to adjust fluid pressure at the pressurized irrigation fluid source 1105 to compensate for flow losses (e.g. incision leakage).

In a further embodiment of the present invention, incision leakage may be determined as the difference between irrigation fluid flow and aspiration fluid flow. Irrigation fluid flow can be measured directly with a flow sensor, can be calculated using a differential pressure measurement, or can be calculated based on plate travel. Readings from the source pressure sensor 1110 and the irrigation pressure sensor 1130 can be used to make a differential pressure measurement. In this case, the flow impedance between the source pressure sensor 1110 and the irrigation pressure sensor 1130 is known (or can be measured). The difference in the pressure readings measured by the source pressure sensor 1110 and the irrigation pressure sensor 1130 can be calculated and flow determined. In the case of plate travel, flow can be estimated from the position and/or movement of the plates 1106 and 1107.

Aspiration fluid flow can also be calculated using a differential pressure measurement. Flow can be calculated by the difference between the measured aspiration pressure at the aspiration pressure sensor 1160, the maximum vacuum that can be created by the pump 1170, and the pump impedance. The impedance of the pump 1170 is a known parameter and the maximum vacuum that the pump creates can be measured accurately as can the aspiration pressure (by the aspiration pressure sensor 1160). In this manner, flow is estimated by the difference in two pressures in the fluid path and the impedance of that path. In this case, the two pressures are the pressure measure by the aspiration pressure sensor 1160 and the maximum pressure achievable by the pump 1170. The impedance in this example is the impedance of the pump 1170.

Using the calculated values for irrigation flow and aspiration flow, one can find incision leakage as the difference between irrigation flow and aspiration flow. This calculation of incision leakage may then be used to more accurately determine the compensation factor. In one embodiment of the of the present invention, the compensation factor is determined dynamically based in part on the calculated incision leakage.

Finally, it should be noted that the position of plates 1106 and 1107 may be used to indicate the volume of fluid used during the procedure left in the flexible bag 1109. As noted above, the relative position of opposing plates 1106 and 1107 indicates the volume of fluid that has exited the flexible bag 1109. In some cases, a new bag of irrigation fluid may need to be installed in pressurized irrigation fluid source 1105 if the existing flexible bag 1109 is low on fluid. Since the relative position of the opposing plates 1106 and 1107 indicates the volume of fluid used, and since the total volume of fluid in flexible bag 1109 is known, these two parameters can be used to provide an indication to the surgeon of the fluid level in the flexible bag 1109 (for example, by displaying fluid level on the display 1220). If the fluid level is low, a warning can be given to the surgeon so that a new flexible bag 1109 of fluid can be installed in pressurized irrigation fluid source 1105.

From the above, it may be appreciated that the present invention provides an improved phacoemulsification system. The present invention provides active control of pressure in the eye during the surgical procedure. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical system comprising:
   a pressurized irrigation fluid source comprising a flexible bag located between two opposing plates; and
   a controller for controlling the pressurized irrigation fluid source;
   wherein the controller controls the pressurized irrigation fluid source based on an estimated flow value modified by a compensation factor, the compensation factor based on compression of an irrigation sleeve that restricts flow of irrigation fluid; and
   wherein the controller calculates the estimated flow value based on travel or motion of the two opposing plates.

2. The surgical system of claim 1 wherein the compensation factor is further based on incision leakage.

3. The surgical system of claim 1 further comprising:
   a display; and
   a controller input device.

4. The surgical system of claim 3 wherein the controller input device receives a desired intraocular pressure value and the controller controls the pressurized irrigation fluid source so as to maintain the desired intraocular pressure value.

5. The surgical system of claim 3 wherein the controller input device receives a desired intraocular pressure range and the controller controls the pressurized irrigation fluid source so as to maintain the desired intraocular pressure range.

6. The surgical system of claim 3 wherein the controller input device receives the compensation factor from a user.

7. The surgical system of claim 3 wherein the controller input device receives needle and sleeve information and the controller uses the needle or sleeve information to select or calculate the compensation factor.

8. The surgical system of claim 7 wherein the controller selects or calculates the compensation factor based on fluid flow characteristics of a needle and sleeve combination.

9. The surgical system of claim 1 wherein the controller calculates intraocular pressure of an eye based on a reading from an irrigation pressure sensor located at or along the pressurized irrigation fluid source or an irrigation line.

10. The surgical system of claim 1 wherein the controller calculates intraocular pressure of an eye based on the estimated flow value.

11. The surgical system of claim 1 wherein the controller calculates intraocular pressure of an eye based on irrigation line impedance.

12. The surgical system of claim 1 further comprising:
    an aspiration line fluidly coupled to a hand piece;
    an aspiration pressure sensor located at or along the aspiration line; and
    an aspiration pump configured to draw fluid through the aspiration line.

13. The surgical system of claim 12 wherein the controller uses a reading from the aspiration pressure sensor to determine if an occlusion is present or if an occlusion break occurs.

14. The surgical system of claim 13 wherein the controller controls the pressurized irrigation fluid source to accommodate for changes in fluid flow that result from the occlusion or the occlusion break.

15. The surgical system of claim 1 wherein the controller calculates intraocular pressure of an eye based on a reading from a source pressure sensor.

16. The surgical system of claim 1 wherein the compensation factor is based on a needle and sleeve selected for a procedure.

* * * * *